US008820608B2

(12) United States Patent
Miyamoto

(10) Patent No.: US 8,820,608 B2
(45) Date of Patent: Sep. 2, 2014

(54) MEDICAL INSTRUMENT

(71) Applicant: Olympus Medical Systems Corp., Tokyo (JP)

(72) Inventor: Manabu Miyamoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/915,995

(22) Filed: Jun. 12, 2013

(65) Prior Publication Data

US 2014/0021240 A1 Jan. 23, 2014

Related U.S. Application Data

(63) Continuation of application No. PCT/JP2012/079368, filed on Nov. 13, 2012.

(60) Provisional application No. 61/560,432, filed on Nov. 16, 2011.

(51) Int. Cl.
*A61B 17/068* (2006.01)
*A61B 17/08* (2006.01)

(52) U.S. Cl.
USPC ....... 227/180.1; 227/19; 227/176.1; 606/153; 606/205; 606/219

(58) Field of Classification Search
USPC .............. 227/19, 176.1, 180.1, 178.1, 175.1, 227/175.2; 606/139, 151, 153, 157, 205, 606/207, 219
See application file for complete search history.

(56) References Cited

U.S. PATENT DOCUMENTS

| 5,605,273 | A | * | 2/1997 | Hamblin et al. | 227/176.1 |
| 5,626,607 | A | * | 5/1997 | Malecki et al. | 606/205 |
| 5,658,300 | A | * | 8/1997 | Bito et al. | 606/143 |
| 6,478,210 | B2 | * | 11/2002 | Adams et al. | 227/180.1 |

(Continued)

FOREIGN PATENT DOCUMENTS

| JP | 10-258060 A | 9/1998 |
| JP | 2005-323723 A | 11/2005 |

(Continued)

OTHER PUBLICATIONS

International Search Report dated Dec. 11, 2012 issued in PCT/JP2012/079368.

(Continued)

*Primary Examiner* — Scott A. Smith
(74) *Attorney, Agent, or Firm* — Scully, Scott, Murphy & Presser, P.C.

(57) ABSTRACT

A medical instrument includes a first grasping member and a second grasping member that approach and separate from each other, a rotating body that is rotatably installed on a rotation shaft fixed to the first grasping member, an open-close link whose first end is rotatably connected to a first rotation shaft provided on the second grasping member and whose second end is rotatably connected to a second rotation shaft provided on the rotating body at a distance from the rotation shaft, and a manipulating member rotating the rotating body. When the rotating body is rotated in a predetermined direction, the first grasping member and the second grasping member approach each other while the second rotation shaft approaches an imaginary straight line connecting axes of the rotation shaft and the first rotation shaft.

9 Claims, 15 Drawing Sheets

(56) References Cited

U.S. PATENT DOCUMENTS

| | | | |
|---|---|---|---|
| 6,488,196 B1 * | 12/2002 | Fenton, Jr. | 227/175.1 |
| 6,843,403 B2 * | 1/2005 | Whitman | 227/176.1 |
| 7,097,650 B2 * | 8/2006 | Weller et al. | 606/153 |
| 7,845,538 B2 * | 12/2010 | Whitman | 227/180.1 |
| 7,914,543 B2 * | 3/2011 | Roth et al. | 606/153 |
| 8,007,505 B2 * | 8/2011 | Weller et al. | 606/153 |
| 8,454,503 B2 * | 6/2013 | Roth et al. | 600/206 |
| 2008/0188891 A1 | 8/2008 | Frank et al. | |
| 2010/0069935 A1 | 3/2010 | Crainich | |
| 2010/0130990 A1 | 5/2010 | Saliman | |
| 2011/0186614 A1 | 8/2011 | Kasvikis | |

FOREIGN PATENT DOCUMENTS

| | | |
|---|---|---|
| JP | 2007-301692 A | 11/2007 |
| JP | 2010-522035 A | 7/2010 |
| WO | WO 2008/118728 A1 | 10/2008 |

OTHER PUBLICATIONS

Notice of Reasons for Rejection dated Jul. 30, 2013 from related Japanese Patent Application No. 2013-526254, together with an English language translation.

* cited by examiner

MEDICAL INSTRUMENT

The present application is a Continuation of International Patent Application No. PCT/JP2012/079368 filed on Nov. 13, 2012, claiming priority on U.S. Provisional Patent Application No. 61/560,432 filed on Nov. 16, 2011, the contents of said U.S. Provisional Patent Application and said PCT Application being incorporated herein.

BACKGROUND OF THE INVENTION

1. Field of the Invention

The present invention relates, in general, to a medical instrument and, more particularly, to a medical instrument having a clamping mechanism.

2. Description of Related Art

Conventionally, a clamping mechanism that opens or closes a pair of jaws is used in a variety of medical instruments. As an example of such a medical instrument, a surgical stapler having a pair of jaws is disclosed in Published Japanese Translation No. 2010-522035 of the PCT International Publication. One of the pair of jaws is mounted with a staple magazine in which staples are charged. The other jaw is mounted with an anvil member having a plurality of staple pockets. When tissue is sandwiched between the pair of jaws and the jaws are closed, the tissue can be sutured by the staples.

When the suturing is conducted using the staples, it is necessary to sufficiently compress the tissue. Further, it is necessary to press the staple against the anvil member and to sufficiently deform the staple. Therefore, it is necessary to close the pair of jaws with a relatively large amount of force.

SUMMARY OF THE INVENTION

According to a first aspect of the present invention, there is provided a medical instrument, which includes: a first grasping member and a second grasping member configured to approach and separate from each other; a rotating body configured to be rotatably installed on a rotation shaft fixed to the first grasping member; an open-close link whose first end is rotatably connected to a first rotation shaft provided on the second grasping member and whose second end is rotatably connected to a second rotation shaft provided on the rotating body at a distance from the rotation shaft; and a manipulating member configured to rotate the rotating body. When the rotating body is rotated in a predetermined direction, the first grasping member and the second grasping member approach each other while the second rotation shaft approaches an imaginary straight line connecting axes of the rotation shaft and the first rotation shaft.

According to a second aspect of the present invention, in the medical instrument relating to the first aspect, the rotating body may be a disc-shaped pulley.

According to a third aspect of the present invention, the medical instrument relating to the first aspect may further include: an insertion unit that has flexibility, and configured to extend along a longitudinal axis and be connected to a proximal end of the first grasping member and a proximal end of the second grasping member; and a manipulation unit provided on a proximal end of the insertion unit. The manipulating member may have flexibility, be disposed in the insertion unit, and be connected to the rotating body and the manipulation unit.

According to a fourth aspect of the present invention, the medical instrument relating to the second aspect may further include: an insertion unit that has flexibility, and configured to extend along a longitudinal axis and be connected to a proximal end of the first grasping member and a proximal end of the second grasping member; and a manipulation unit provided on a proximal end of the insertion unit. The manipulating member may have flexibility, be disposed in the insertion unit, and be connected to the rotating body and the manipulation unit.

According to a fifth aspect of the present invention, the medical instrument relating to the first aspect may further include a grasping member link whose first end is rotatably connected to first rotation shaft and whose second end is rotatably connected to a third rotation shaft provided on the first grasping member. When the rotating body is rotated in a predetermined direction, the first grasping member and the second grasping member may approach each other while a distance between an intersection, at which an imaginary straight line connecting the axis of the first rotation shaft and an axis of the second rotation shaft intersects an imaginary straight line connecting an axis of the third rotation shaft and the axis of the rotation shaft, and the axis of the rotation shaft is reduced.

According to a sixth aspect of the present invention, in the medical instrument relating to the fifth aspect, the first grasping member may be fixed to target tissue for treatment. The second grasping member may approach the first grasping member by moving to a proximal end side of the first grasping member.

According to a seventh aspect of the present invention, the medical instrument relating to the first aspect may further include a holder configured to hold a proximal end of the second grasping member at a predetermined position when the first grasping member and the second grasping member approach each other.

According to an eighth aspect of the present invention, the medical instrument relating to the fifth aspect may further include a position unit configured to position the first grasping member and the second grasping member in a predetermined positional relation when the first grasping member and the second grasping member approach each other.

According to a ninth aspect of the present invention, in the medical instrument relating to the eighth aspect, the position unit may include: a first contacting face configured to be provided on the first grasping member; and a second contacting face configured to be provided on the second grasping member and come into contact with the first contact face when the first grasping member and the second grasping member approach each other.

According to a tenth aspect of the present invention, the medical instrument relating to the first aspect may further include a manipulation unit to which the manipulating member is connected and to which manipulation of rotating the rotating body is input.

According to an eleventh aspect of the present invention, in the medical instrument relating to the fifth aspect, the first grasping member may have a cartridge that contains staples and is exchangeably installed. The first grasping member and the second grasping member may function as a stapler.

According to a twelfth aspect of the present invention, in the medical instrument relating to the eighth aspect, the first grasping member may have a cartridge that contains staples and is exchangeably installed. The first grasping member and the second grasping member may function as a stapler.

DETAILED DESCRIPTION OF THE INVENTION

First Embodiment

Hereinafter, a medical instrument relating to a first embodiment of the present invention will be described with reference to FIGS. 1 to 11.

Figure 1:
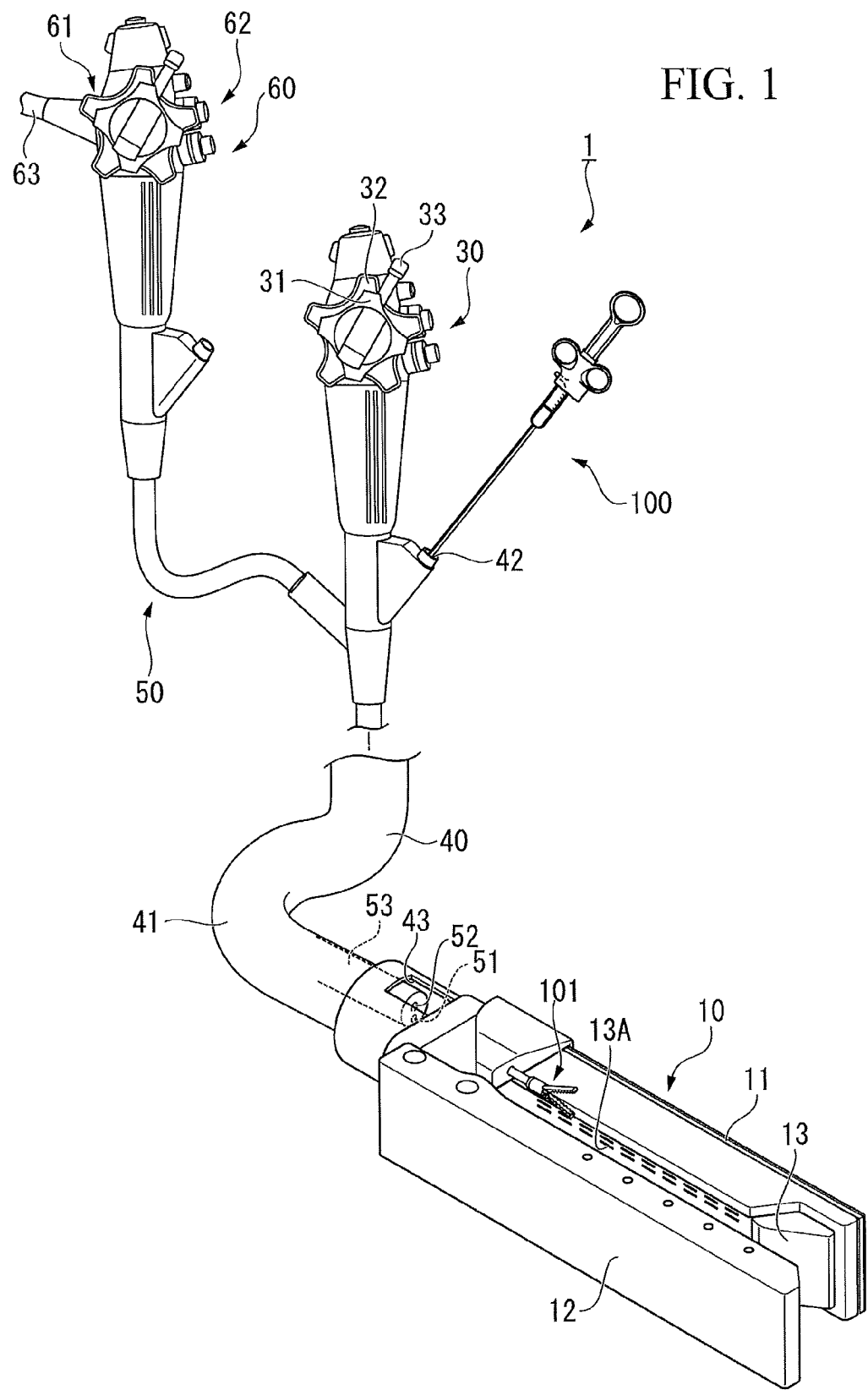
FIG. 1 is a view showing an entire constitution of a medical instrument relating to a first embodiment of the present invention.

FIG. 1 is a view showing an entire constitution of a medical instrument 1 relating to the present embodiment. The medical instrument 1 includes a clamping mechanism relating to the present embodiment. The medical instrument 1 includes a treatment unit 10 that is provided at a distal end thereof and for conducting treatment on target tissue. The medical instrument 1 may further include a first manipulation unit 30 for manipulating the treatment unit 10, an insertion unit 40 installed between the treatment unit 10 and the first manipulation unit 30, an observation unit 50 inserted into the insertion unit 40, and a second manipulation unit 60 for manipulating the observation unit 50. The treatment unit 10 has a first jaw (first grasping member) 11 and a second jaw (second grasping member) 12 as a pair of jaws that can be opened and closed. The treatment unit 10 also has a pulley (rotating body) 17, a wire (manipulating member) 18, and open-close links 19. The treatment unit 10 sutures and incises tissue using a cartridge 13 loaded with staples 13A, and a basic structure thereof is known as set forth in, for instance, Published Japanese Translation No. 2010-522035 of the PCT International Publication as described above. Features of the treatment unit 10 relating to the present embodiment will be described below in detail.

The first manipulation unit 30 has a known constitution and includes two dial knobs 31 and 32 and a lever 33. The dial knob 31 is connected to the treatment unit 10 by a manipulating member (which will be described below) such as a wire. As the dial knob 31 is rotated, opening-closing manipulation can be conducted on the pair of jaws 11 and 12.

The insertion unit 40 has flexibility and is formed in a tubular shape. The insertion unit 40 is constituted so that the treatment unit 10 is installed at a distal end side thereof and the first manipulation unit 30 is installed at a proximal end side thereof. The insertion unit 40 is provided with a curved unit 41 at the distal end side thereof which has a known structure with a plurality of knob rings or curved tips. The curved unit 41 can be bent by manipulating the dial knob 32 of the first manipulation unit 30. The manipulating member is inserted into a cavity of the insertion unit 40 so as to be able to advance or retreat in an axial direction. A forceps hole 42 is provided at the proximal end side of the insertion unit 40. A common treatment tool 100 for an endoscope having a forceps unit 101 can be inserted into the forceps hole 42 and protrude from the proximal end side of the first jaw 11.

The observation unit 50 is inserted into the insertion unit 40 so as to be able to advance or retreat. The observation unit 50 is provided with a lighting unit 51 including a light emitting diode (LED) and an image capturing means 52 such as a charge-coupled device (CCD) at a distal end thereof. The observation unit 50 is provided with a curved unit 53 at a distal end side thereof which has a structure similar to that of the curved unit 41. The distal end of the observation unit 50 can protrude from and sink into an opening hole 43 provided at the distal end side of the insertion unit 40.

The second manipulation unit 60 is connected to the proximal end of the observation unit 50 coming out of the proximal end side of the insertion unit 40. The second manipulation unit 60 is provided with a dial knob 61 as in the first manipulation unit 30 and a button 62. The second manipulation unit 60 can conduct the bending manipulation of the curved unit 53 and manipulations of the lighting unit 51 and the image capturing means 52. A video signal acquired by the image capturing means 52 is transmitted to an image processing unit (not shown) through a universal cable 63 and is displayed on a display (not shown). As the observation unit 50 and the second manipulation unit 60, known endoscopic devices can be used by appropriately setting dimensions.

Figure 2:
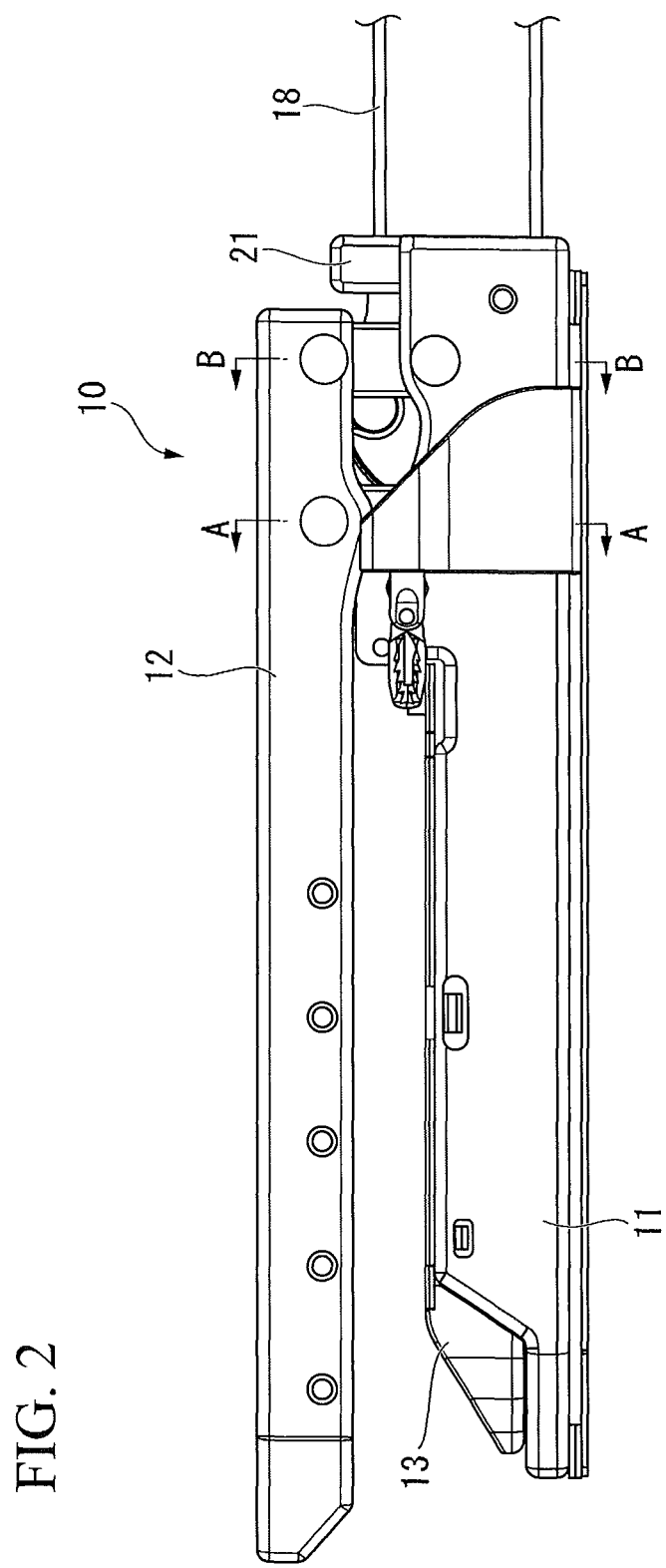
FIG. 2 is an enlarged view of a treatment unit of the medical instrument relating to the first embodiment of the present invention.
Figure 3:
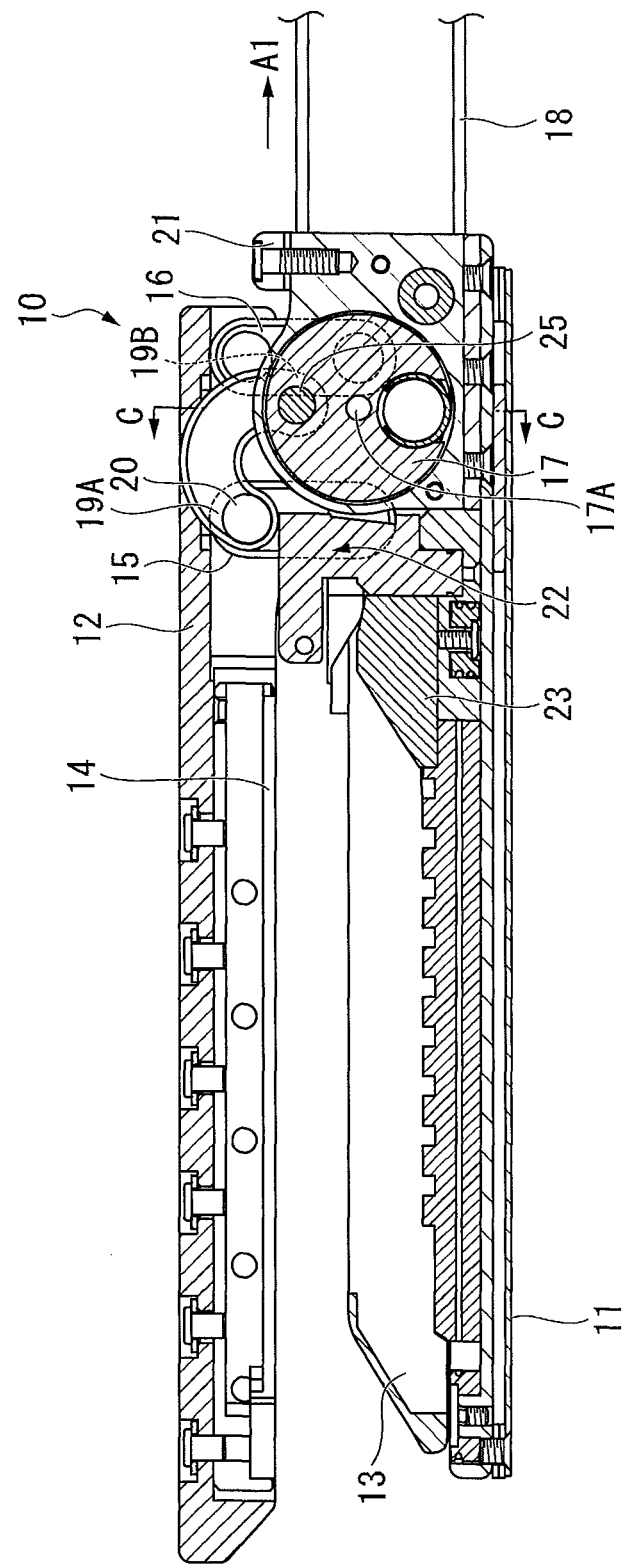
FIG. 3 is a sectional view taken in a longitudinal direction of the treatment unit of the medical instrument relating to the first embodiment of the present invention.

FIG. 2 is an enlarged view of the treatment unit 10. FIG. 3 is a sectional view taken in a longitudinal direction of the treatment unit 10. As shown in FIG. 2, the cartridge 13 on which a plurality of rows of staples 13A are loaded side by side in a longitudinal direction is exchangeably mounted on the first jaw 11. As shown in FIG. 3, a cutter 22 and a wedge 23 that are able to advance or retreat between the rows of the staples 13A are installed on the first jaw 11. The cutter 22 can advance or retreat by manipulation of the lever 33 of the first manipulation unit 30. An anvil member 14 bending a distal end of each staple 13A is installed on the second jaw 12.

Figure 4:
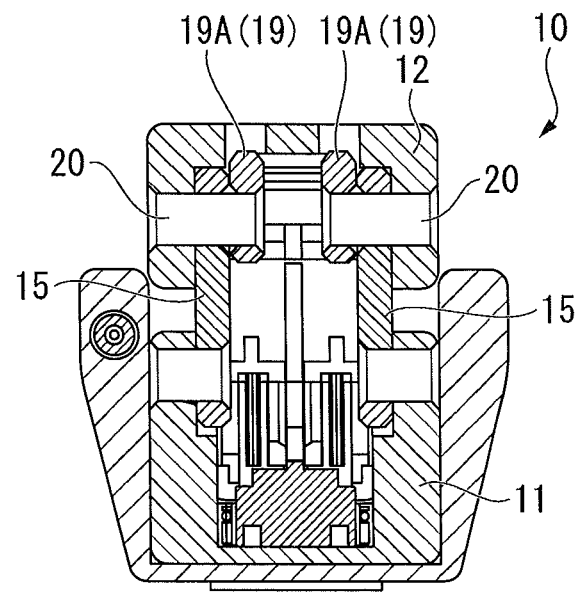
FIG. 4 is a cross-sectional view taken along line A-A of FIG. 2.
Figure 5:
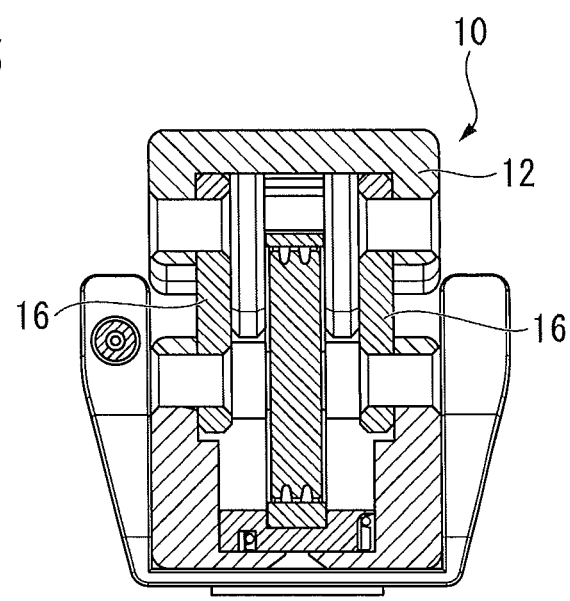
FIG. 5 is a cross-sectional view taken along line B-B of FIG. 2.

FIGS. 4 and 5 are cross-sectional views taken along lines A-A and B-B of FIG. 2, respectively. As shown in FIGS. 4 and 5, the first jaw 11 and the second jaw 12 are connected by a pair of parallel links (grasping member links) 15 and 16, respectively. That is, the first jaw 11 and the second jaw 12 are connected by four parallel links. The first jaw 11 and the second jaw 12 can approach and separate from each other while maintaining a state in which they are parallel to each other.

Figure 6:
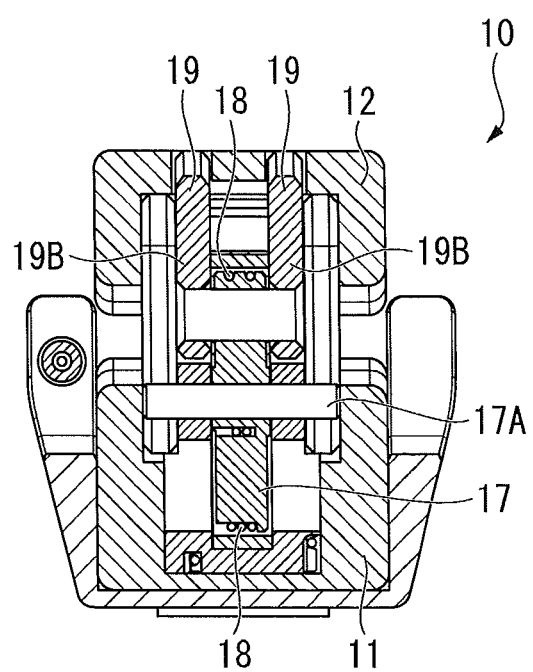
FIG. 6 is a cross-sectional view taken along line C-C of FIG. 3.

FIG. 6 is a cross-sectional view taken along line C-C of FIG. 3. As shown in FIGS. 3 and 6, a pulley (rotating body) 17 for conducting opening-closing manipulation on the first jaw 11 and the second jaw 12 is disposed on the proximal end side of the treatment unit 10. The pulley 17 is rotatably mounted on a rotation shaft 17A installed on the first jaw 11. A wire (manipulating member) 18 is wound on the pulley 17. An end of the wire 18 is connected to the dial knob 31 of the first manipulation unit 30 through the insertion unit 40.

The pulley 17 and the second jaw 12 are connected by a pair of open-close links 19 having an approximate semi-arc shape. One end 19A of each open-close link 19 is rotatably connected to a connecting shaft (first rotation shaft) 20 of the parallel link 15 of the two parallel links, which is disposed at the distal end, and the second jaw 12. The other end 19B is rotatably connected to a rotation shaft (second rotation shaft) 25 installed on the pulley 17.

As shown in FIG. 2, the proximal end of the first jaw 11 is provided with a protrusion (holder) 21 that comes into contact with the second jaw 12 when the pair of jaws 11 and 12 are closed. As shown in FIG. 3, the protrusion 21 is a screw type. A screwed length by which the protrusion 21 and the first jaw 11 are screwed together is adjusted. Thereby, the amount of protrusion from the first jaw 11 can be adjusted to be within a given range.

An operation when the medical instrument 1 constituted as described above is used will be described. First, an operator inserts the distal end side of the medical instrument 1 on which the treatment unit 10 is installed into a natural opening such as the mouth of a patient. The operator introduces the treatment unit 10 up to the vicinity of tissue to be treated while observing the treatment unit 10 and its surroundings using the observation unit 50.

The operator positions tissue to be sutured between the first jaw 11 and the second jaw 12. The operator rotates the dial knob 31 of the first manipulation unit 30 in a predetermined direction and pulls the wire 18 in a direction of an arrow A1 shown in FIG. 3. Then, the pulley 17 is rotated clockwise in FIG. 3. For this reason, the end 19B of the open-close link 19 rotates and moves around the rotation shaft 17A of the pulley 17. In line with the rotational movement, the end 19A and the connecting shaft 20 also move to the proximal end side. Thereby, connecting sites of the parallel links 15 and 16 and the second jaw 12 move to the proximal end side. As a result, the second jaw 12 maintains a state in which it is parallel with the first jaw 11 and approaches the first jaw 11 while moving to the proximal end side relative to the first jaw 11 fixed to the tissue to be treated. Thus, the pair of jaws are closed.

In this case, in line with the rotation of the pulley 17, the rotation shaft 25 approaches an imaginary line connecting the rotation shaft 17A and the connecting shaft 20. In other words, the clamping mechanism relating to the present embodiment in which the pair of jaws 11 and 12 connected by the parallel links 15 and 16 are closed by the rotation of the pulley 17 subjected to manipulation input via the wire 18 is understood to function as a so-called toggle mechanism (a step-up mechanism or a boosting mechanism).

Figure 7:
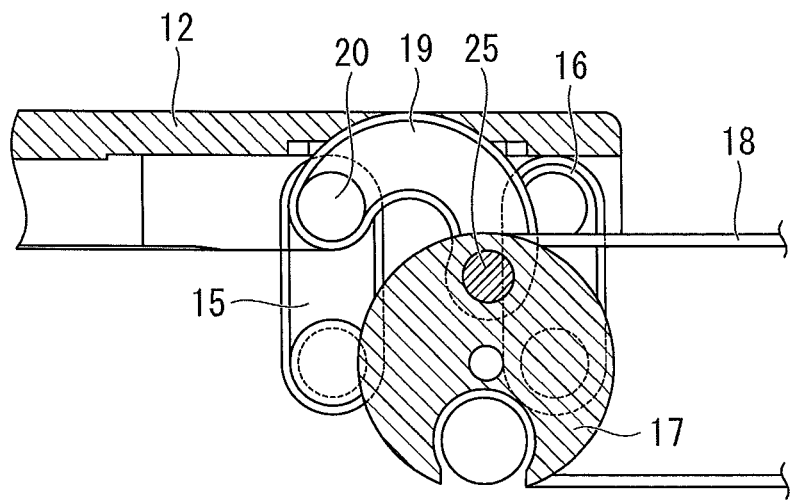
FIG. 7 is a view showing the force applied to each unit when a pair of jaws of the treatment unit of the medical instrument relating to the first embodiment of the present invention are closed.
Figure 8:
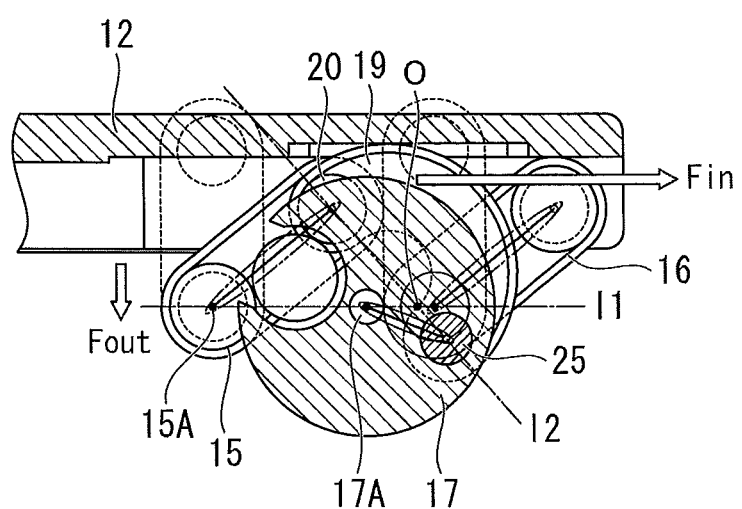
FIG. 8 is a view showing a force applied to each unit when the pair of jaws of the treatment unit of the medical instrument relating to the first embodiment of the present invention are closed.

FIGS. 7 and 8 are views for describing a force applied to each unit when the pair of jaws 11 and 12 are closed. It is considered that the wire 18 is pulled from an initial state shown in FIG. 7, and the second jaw 12 approaches the first jaw 11 as shown in FIG. 8. Here, an intersection of a straight line 11, which connects the rotation shaft 17A and a connecting point (third rotation shaft) 15A of the parallel link 15 and the first jaw 11, and a straight line 12, which connects the axes of the connecting shaft 20 and the rotation shaft 25, is defined as O. A line segment connecting the rotation shaft 17A and the intersection O is defined as OA. A line segment connecting the connecting point 15A and the intersection O is defined as OB. In the parallel link 15, a length between the connecting point 15A and the axis of the connecting shaft 20 is defined as L1. An angle at which the parallel link 15 forms a parallel plane with the first jaw 11 at the proximal end side is defined as θ. A radius of the pulley 17 is defined as R. In this case, in the event of the closing manipulation of the pair of jaws, a relation between a pulling force Fin of the wire 18 and a force Fout applied to the second jaw 12 in a direction in which the second jaw 12 approaches the first jaw 11 is expressed by the following equation.

$$F\text{out} = (\overline{OB}/\overline{OA}) \cdot (1/L1 \cos \theta) \cdot R \cdot F\text{in}$$

Therefore, when the wire 18 is pulled in a direction of an arrow A1, the length of the line segment OA is gradually reduced to approach zero as the straight line 12 approaches the rotation shaft 17A. As a result, since Fout is increased, a grasping force of the pair of jaws can be further increased.

Figure 9A:
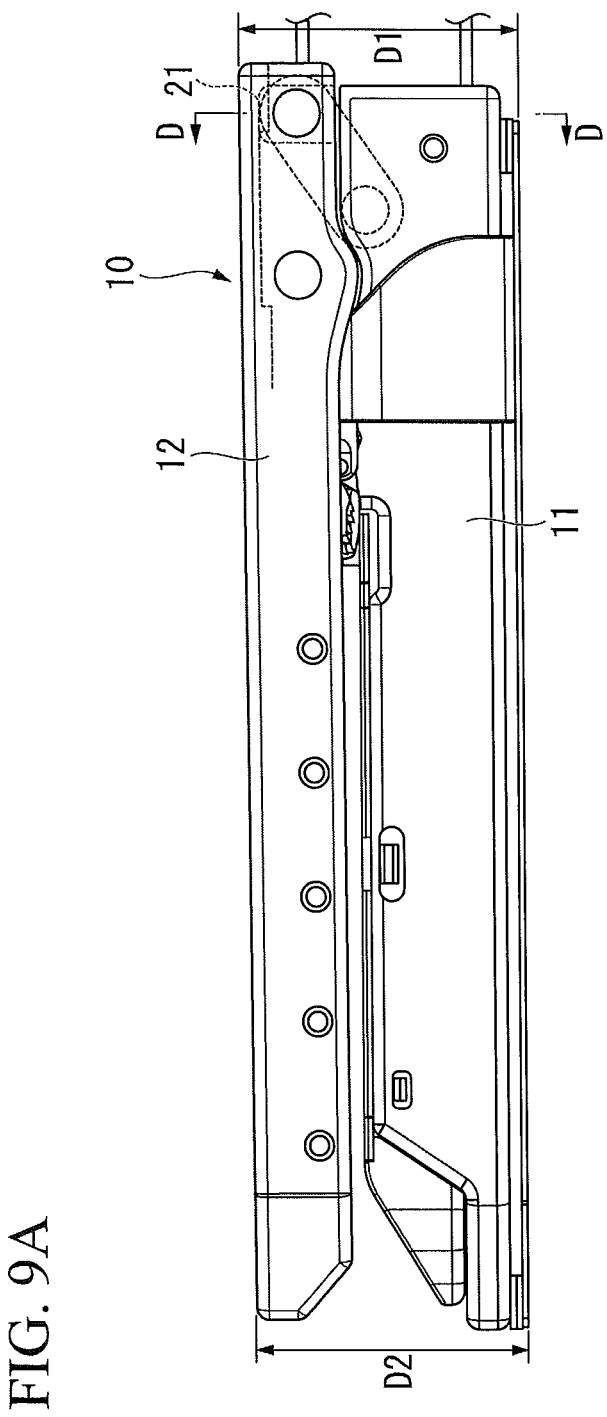
FIG. 9A a view showing a state in which the pair of jaws of the treatment unit of the medical instrument relating to the first embodiment of the present invention are closed.
Figure 9B:
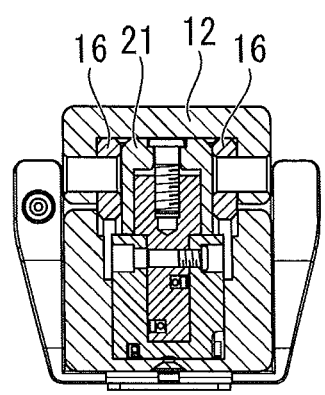
FIG. 9B is a cross-sectional view taken along line D-D of FIG. 9A.

When the pulley 17 is rotated at a predetermined amount or more, this toggle mechanism is broken. However, when the pair of jaws 11 and 12 are closed as shown in FIG. 9A, the proximal end of the second jaw 12 comes into contact with the protrusion 21 of the first jaw 11 as shown in FIG. 9B. For this reason, the pulley 17 cannot be rotated at the predetermined amount or more, the breakdown of the toggle mechanism is prevented. Further, the protruding length of the protrusion 21 is set in such a manner that, when the proximal end of the second jaw 12 comes into contact with the protrusion 21, the second jaw 12 is slightly inclined, and a height dimension D1 at the proximal end side of the treatment unit 10 is slightly higher than a height dimension D2 at the distal end side. Thereby, the proximal end side of the second jaw 12 is held at a predetermined position. Furthermore, a situation in which even though a sufficient closing force is applied to the pair of jaws, only the distal end side is opened due to the reaction force received from the grasped tissue is prevented.

If the tissue is reliably grasped between the pair of jaws 11 and 12, the operator manipulates the lever 33 to advance the cutter 22. Then, the wedge 23 forces the staples 13A in the cartridge 13 to be pressed to the anvil member 14 and to be bent by a known mechanism, and thereby the tissue is sutured. Furthermore, the cutter 22 cuts off the tissue between the rows of the staples suturing the tissue, and the target tissue is incised without generating a perforation.

When the insertion unit having flexibility is provided as in the medical instrument 1 relating to the present embodiment, a flexible member such as a wire should also be used as the manipulating member. However, because such a manipulating member is low in breaking load and is subjected to a transfer loss by friction against the insertion unit, it is not easy to increase the amount of force applied to the treatment unit. Especially, in a stapler like the treatment unit 10, the amount of force applied to the treatment unit is very high, ranging from hundreds to thousands of Newtons. For this reason, it is difficult to generate the amount of force required for the treatment unit using the flexible manipulating member. If the amount of force is deficient, there is a possibility of the tissue dropping out from between the pair of jaws when the cutter is advanced or of not being able to realize appropriate stapling because compression of the tissue becomes insufficient. As a result, there is a problem that it is difficult to conduct a stable procedure.

To solve these, increasing a speeding reduction ratio using a worm gear or a ball screw disposed in the vicinity of the treatment unit may also be considered. However, in this structure, since the speed reduction ratio is constantly great, a great amount of force is not required for the treatment unit. Even when clipping the tissue is begun, a stroke of the manipulating member is increased. For this reason, especially, a manual case has a problem in that the manipulation is not easy.

In the medical instrument 1 relating to the present embodiment, as described above, the clamping mechanism made up of the pulley 17, the open-close links 19, and the parallel links 15 and 16 functions as the toggle mechanism. For this reason, even when the flexible member such as the wire is used as the manipulating member rotating the pulley, a great grasping force can be generated between the pair of jaws by increasing the speed reduction ratio in the vicinity of the treatment unit. Thus, the flexible insertion unit is provided to enable the approach to the target tissue from the natural opening, and the tissue is reliably grasped between the pair of jaws so that the suture based on the staple and the excision of tissue can be appropriately conducted.

The speed reduction ratio is not increased until the pair of jaws are closed. For this reason, in the beginning of clipping the tissue, an amount of manipulation of the manipulating member may be reduced, and a manipulation feeling is not impaired. As the tissue is grasped and thinned by compression, the speed reduction ratio is increased. As such, the operator can always conduct the manipulation with a minimum necessary amount of pulling of the manipulating member.

After the pair of jaws are completely closed, even when the hand is separated from the dial knob 31, the toggle mechanism works, and thereby the closed state is maintained. As long as the pulley 17 is not rotated, the pair of jaws are not opened. Thus, it is not necessary to continue to add the manipulation input to the manipulating member in order to maintain the closed state of the jaws. For this reason, the burden of the operator during the manipulation can be reduced.

An amount of manipulating force from the first manipulation unit 30 is transmitted to the open-close links 19 using the pulley 17 as an input segment. For this reason, it is not necessary to receive the reaction force, which is caused from the links by the toggle mechanism, at the wire 18. Furthermore, since the pulley 17 is the rotating body, if sufficient rigidity is secured for the rotation shaft 17A, it is not necessary to separately provide a guide regulating a behavior. Thus, the constitution of the connecting sites of the treatment unit and the manipulating member is simplified and easily reduced in size as well.

Even when the opening-closing stroke of the treatment part is increased for an input mechanism using the pulley 17 and the wire 18, it is difficult for a hard length of the distal end of the medical instrument 1 to be increased. As a result, insertability into a body cavity and a size of the opening-closing stroke can be compatible to a high level.

The open-close links 19 are formed in an arc shape. For this reason, interference with the parallel links 15 and 16 is prevented during the opening or closing of the treatment part, and the distance between the ends 19A and 19B can be adjusted to be a desired value.

The pair of jaws are closed while the second jaw 12 of a movable side moves to the proximal end side relative to the first jaw 11 of a stationary side. For this reason, a force is applied to the grasped tissue so as to be attracted to the proximal end side, and the grasped tissue can be appropriately inhibited from dropping out from between the jaws.

Figure 10:
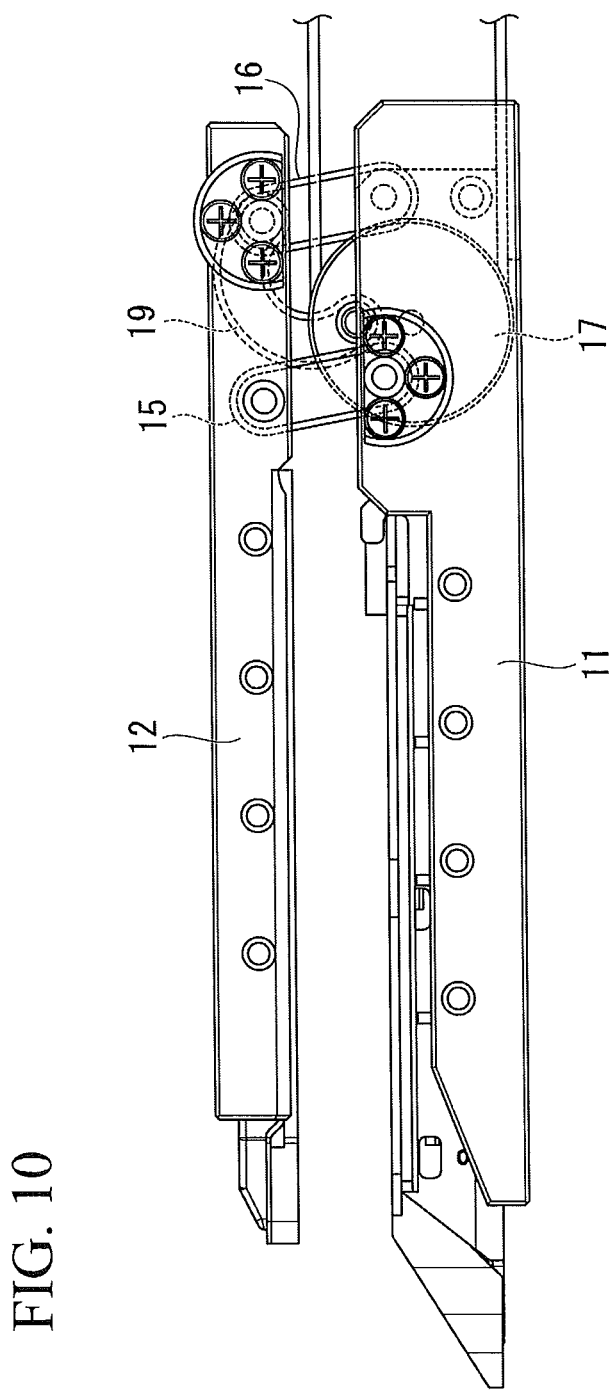
FIG. 10 is a view showing a treatment unit of a modification of the medical instrument relating to the first embodiment of the present invention.
Figure 11:
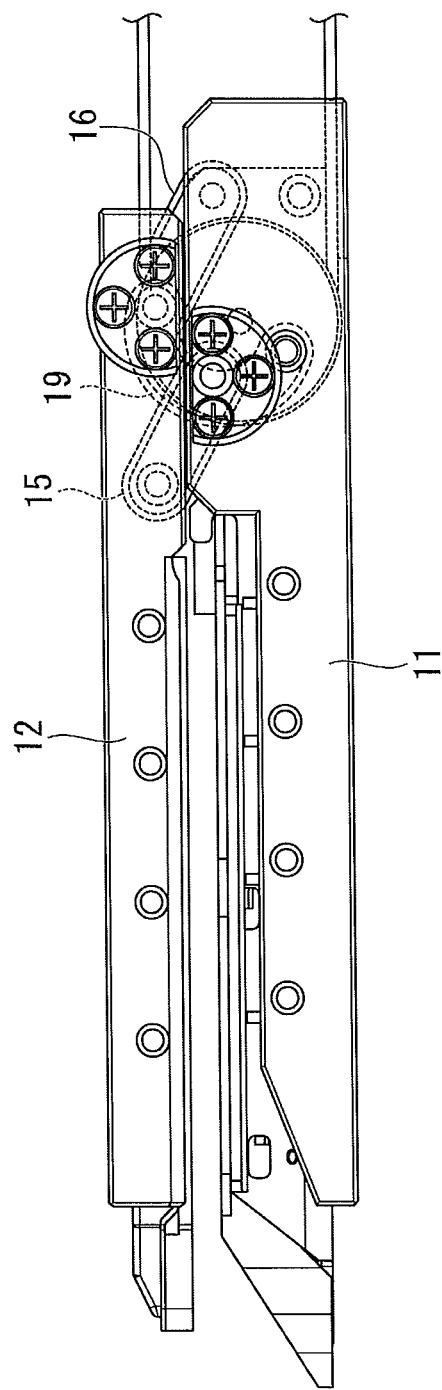
FIG. 11 is a view showing the treatment unit of the modification of the medical instrument relating to the first embodiment of the present invention.

The clamping mechanism relating to the present embodiment is not limited to the constitution described above. As shown in FIG. 10, the open-close link 19 and the parallel link 16 of the proximal end side may be connected to reverse an installed relation between the open-close link and the parallel link. In this case, as shown in FIG. 11, the second jaw 12 approaches the first jaw 11 while moving to the distal end side relative to the first jaw 11, and the pair of jaws are closed. This constitution cannot always be said to be appropriate when the treatment unit is the stapler. However, the constitution can be applied to the treatment unit, which does not have such a restraint, without difficulty. The grasping force of the treatment part can be suitably increased.

Second Embodiment

A medical instrument relating to a second embodiment of the present invention will be described with reference to FIGS. 12 and 13. The present embodiment is different from the first embodiment in that the treatment unit is formed in the grasping forceps having the pair of jaws. In the following description, the same reference numerals are given to constitutions similar to those described previously, and duplicate description will be omitted here.

Figure 12:
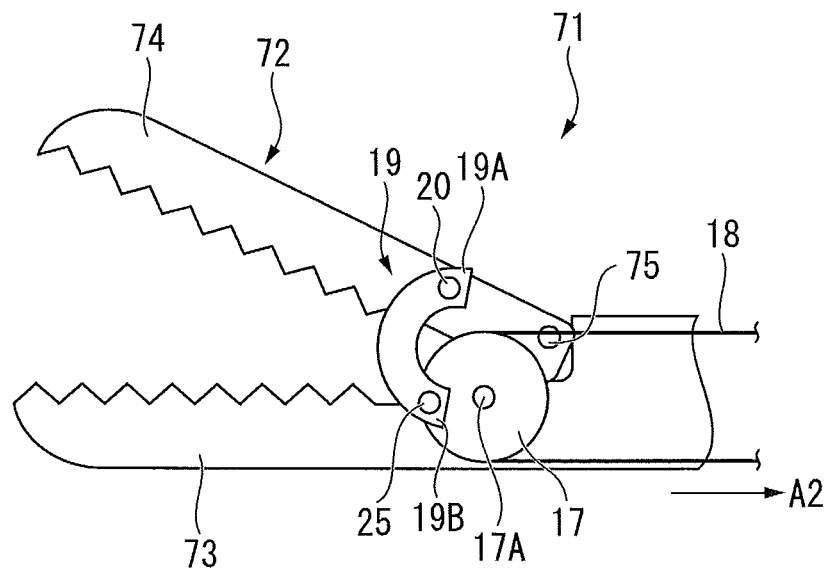
FIG. 12 is a view showing a treatment unit of a medical instrument relating to a second embodiment of the present invention.
Figure 13:
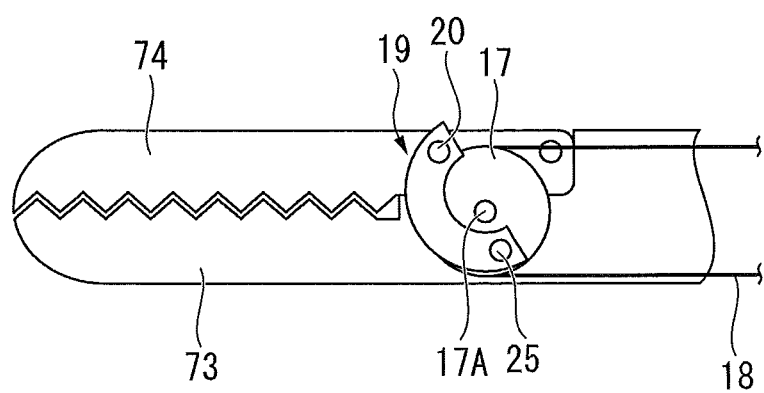
FIG. 13 is a view showing a state in which the treatment unit of the medical instrument relating to the second embodiment of the present invention is closed.

FIG. 12 is an enlarged view of a treatment unit 72 of a treatment tool 71 for an endoscope in the medical instrument relating to the present embodiment. The treatment unit 72 is provided with a pair of a stationary-side jaw 73 and a movable-side jaw 74 that are opened or closed. The stationary-side jaw 73 and the movable-side jaw 74 are connected by a rotation shaft 75 so as to be relatively rotatable. One end 19A of each open-close link 19 is connected to the movable-side jaw 74 at a distal end side from the rotation shaft 75 so as to be relatively rotatable.

In the treatment tool 71 for the endoscope relating to the present embodiment, a pulley 17 is rotated by pulling a wire 18 in a direction of an arrow A2 via a manipulation part (not shown). Then, the movable-side jaw 74 is rotated around the rotation shaft 75 to approach the stationary-side jaw 73. As shown in FIG. 13, the pair of jaws 73 and 74 are closed. Here, in line with the rotation of the pulley 17, a connecting shaft 25 of the end 19B approaches an imaginary straight line connecting a rotation shaft 17A of the pulley and a connecting shaft 20 of the end 19A. That is, the pair of jaws 73 and 74 include a toggle mechanism having a basic structure as in the first embodiment. For this reason, a greater grasping force can be realized by the pair of jaws.

In this manner, the clamping mechanism relating to the present embodiment can be applied to the treatment unit as in the first embodiment which is opened or closed while maintaining a parallel state along with the treatment unit connected by one rotation shaft so as to be relatively rotatable without difficulty.

In the present embodiment, a proximal end of the movable-side jaw 74 is fixed to the rotation shaft 75. For this reason, when the distal end side of the movable-side jaw 74 receives a reaction force from grasped tissue to move in an opening direction, it does not approach the stationary-side jaw 73.

That is, the rotation shaft 75 functions as a holder that holds the proximal end of the movable-side jaw 74 at a predetermined position. As a result, the grasping force is increased by the toggle mechanism, and thereby the distal end sides of the pair of jaws can be reliably closed without being influenced by the reaction force.

Although the exemplary embodiments of the present invention have been described, the present invention is not limited to these embodiments. Accordingly, additions, omissions, substitutions, and other modifications of the constitution are possible without departing from the spirit of the present invention.

For example, the case in which the treatment unit is the stapler like the first embodiment is considered. To perform suitable suturing using the staple, it is necessary for the anvil member and the cartridge to be positioned in a predetermined positional relation with high precision. Furthermore, it is necessary for the staple to be pressed against a staple pocket of the anvil member. However, when the pair of jaws are connected using the links, a gap is required between the connecting shaft and the jaw in order to rotatably connect the links and the jaws. This gap causes backlash (deviation from the connecting shaft) during the opening or closing of the pair of jaws.

Figure 14A:
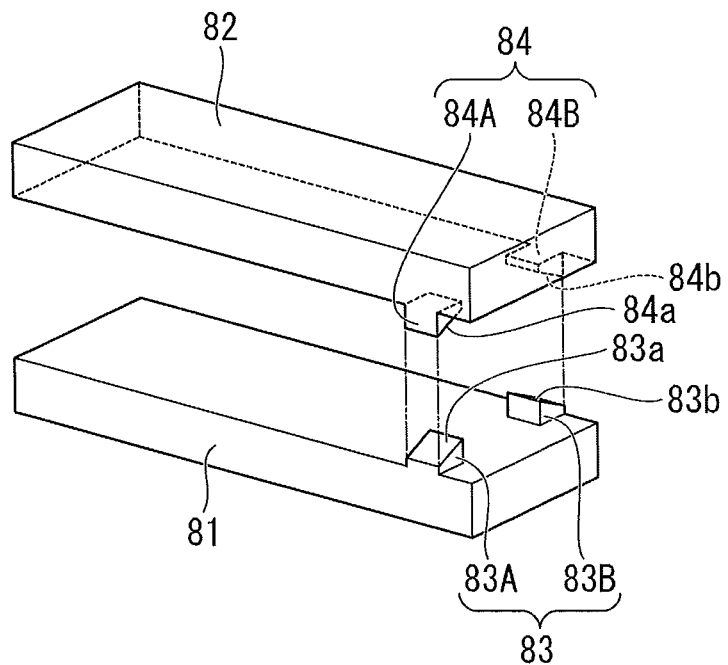
FIGS. 14A, 14B, 14C and 14D are a view showing a pair of jaws in another modification of the medical instrument relating to the first embodiment of the present invention.

Hence, as shown in FIG. 14A, a pair of jaws 81 and 82 may be provided with respective protruding units 83 and 84 as position units. The protruding unit 83 provided for the jaw 81 is constituted of a pair of protrusions of a first protrusion 83A and a second protrusion 83B formed at widthwise opposite sides of the jaw 81. Top faces (first contact faces) of the protrusions 83A and 83B are formed on respective inclined faces 83a and 83b. With the approach to widthwise ends, heights of the protrusions 83A and 83B are lowered. The protruding unit 84 provided for the jaw 82 is constituted of a pair of protrusions including a first protrusion 84A and a second protrusion 84B formed at widthwise opposite sides of the jaw 82. Bottom faces (second contact faces) of the protrusions 84A and 84B are formed on respective inclined faces 84a and 84b having inclined angles corresponding to the inclined faces 83a and 83b. With the approach to widthwise ends, protruding lengths of the protrusions 84A and 84B are increased.

In this way, when the jaw 81 and the jaw 82 approach each other, the inclined face 83a and the inclined face 84a come into contact with each other, and the inclined face 83b and the inclined face 84b come into contact with each other. Thereby, first, the jaw 81 and the jaw 82 are positioned in a parallel state. When offset caused by backlash takes place in the widthwise direction of the pair of jaws 81 and 82, the jaw 81 and the jaw 82 relatively move parallel to the inclined faces 83a and 83b with the approach to each other, and the offset is corrected. Finally, the pair of jaws are positioned in the predetermined positional relation without the offset and are closed. Accordingly, even when slight backlash takes place, the pair of jaws can be closed with the cartridge and the anvil member positioned reliably. As a result, the suture can be conducted.

Figure 14B:
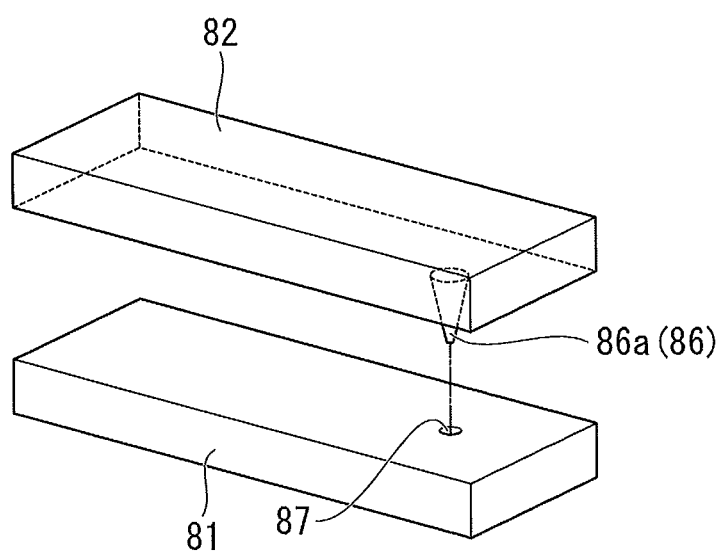

The shape of the position unit is not limited to the foregoing. For example, as shown in FIG. 14B, the position unit may be constituted of a protrusion 86 of an approximately conical shape and a circular hole 87 into which at least a part of the protrusion 86 can enter. In this case, a curved tapered face 86a of the protrusion 86 comes into contact with an upper edge of the hole 87, and the protrusion 86 enters the hole 87. Thereby, the offset is corrected.

Figure 14C:
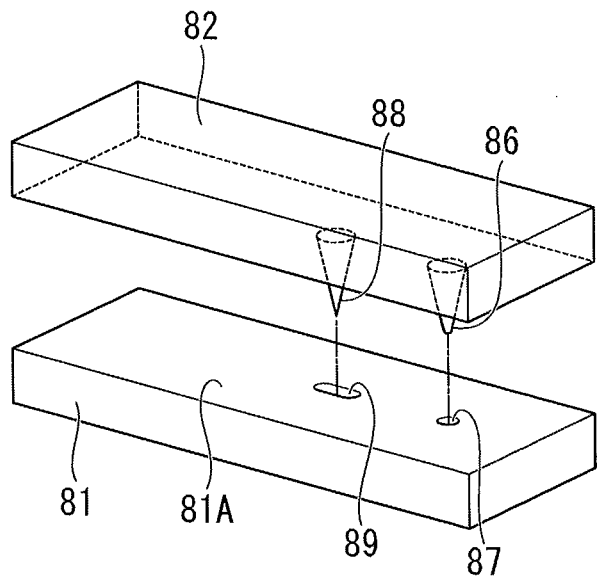

In this case, as further shown in FIG. 14C, a protrusion 88 and an elongate hole 89 may be provided. The protrusion 88 is an approximately conical protrusion whose protruding length is longer than that of the protrusion 86. The elongate hole 89 is an oval elongate hole that extends in a longitudinal direction of the jaw 81 when viewed from the top. In this way, as in the first embodiment, when the jaw 82 approaches the jaw 81 while relatively moving in the longitudinal direction, the protrusion 88 enters the elongate hole 89 first, and the widthwise offset is corrected and suppressed. Afterwards, the protrusion 86 enters the hole 87 and is reliably positioned. Accordingly, more reliable positioning can be conducted.

An inner face of the hole 87 or the elongate hole 89 may be orthogonal to a suture face 81A of the jaw 81. Further, the inner face of the hole 87 or the elongate hole 89 may be inclined so as to correspond to the tapered faces of the protrusions 86 and 88. In the latter case, there is an advantage in that the sliding is made smoother when the pair of jaws approach each other. The disposition of the hole and the protrusion may be reversed, and the protrusions 86 and 88 may be formed on the jaw 81.

Figure 14D:
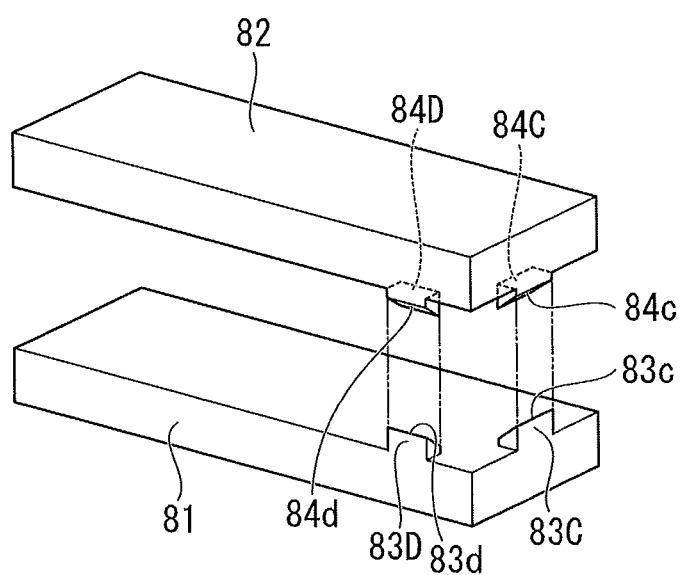

When the protruding unit having the inclined face is formed, a set of protrusions may be formed so as to have inclined faces 83c and 84c that are inclined in a direction orthogonal to the inclined direction of the inclined face 83a, like the protrusions 83C and 84C shown in FIG. 14D. In this way, a longitudinal offset can be also corrected in addition to the widthwise offset. The positioning can be conducted with higher precision. In FIG. 14D, protrusion 83D and 84D formed at the widthwise ends of the pair of jaws have inclined faces 83d and 84d. Inclinations of the inclined faces 83d and 84d are formed reversely with the inclinations of the inclined faces 83a and 84a of the protrusions 83A and 84A. In this way, a positioning effect can be obtained with no problems.

Figure 15:
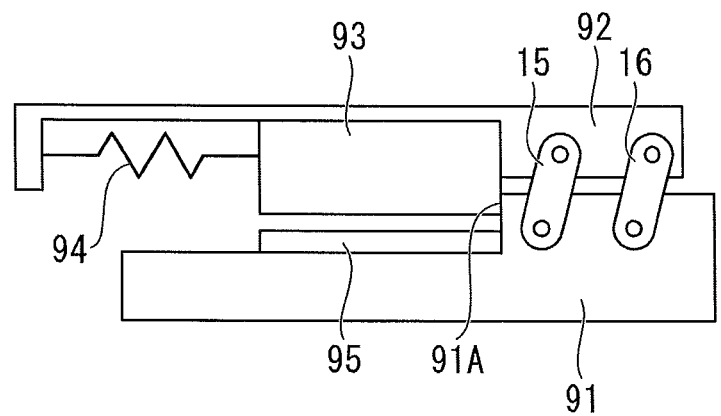
FIG. 15 is a schematic view showing a treatment unit in another modification of the medical instrument relating to the first embodiment of the present invention.
Figure 16:
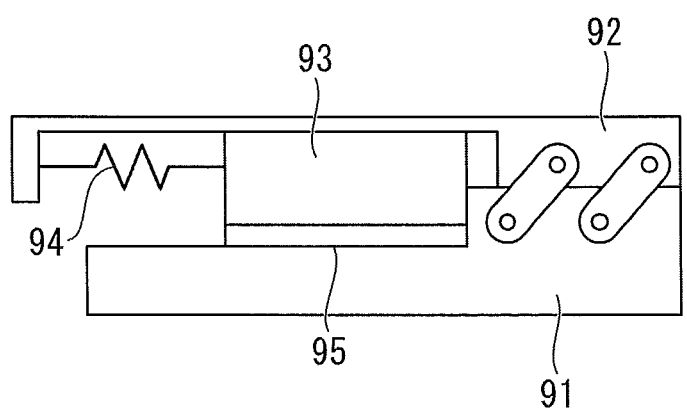
FIG. 16 is a schematic view showing a treatment unit in another modification of the medical instrument relating to the first embodiment of the present invention.

The position unit is not limited to that having the set of protrusions or the set of the protrusion and hole as described above. In a modification shown in FIG. 15, an anvil member 93 installed on a second jaw 92 is biased by a biasing member 94 such as a spring so as to be in contact with a face 91A of a proximal end side of a first jaw 91 at all times. In this way, as shown in FIG. 16, even when the pair of jaws 91 and 92 are closed while the second jaw 92 moves relative to the first jaw 91, a position of the anvil member 93 is held in contact with the face 91A. For this reason, the anvil member 93 can be appropriately positioned with respect to the cartridge 95.

In this example, the biasing member 94 carries out the longitudinal positioning of the anvil member 93. A similar biasing member may be disposed at widthwise opposite sides or one side of the anvil member and carry out widthwise positioning of the anvil member 93. Both may be combined. In the present modification, as the biasing member, various elastic bodies such as a leaf spring, a disc spring, a tensile spring, a compressive spring, and an elastomer may be appropriately selected.

Figure 17:
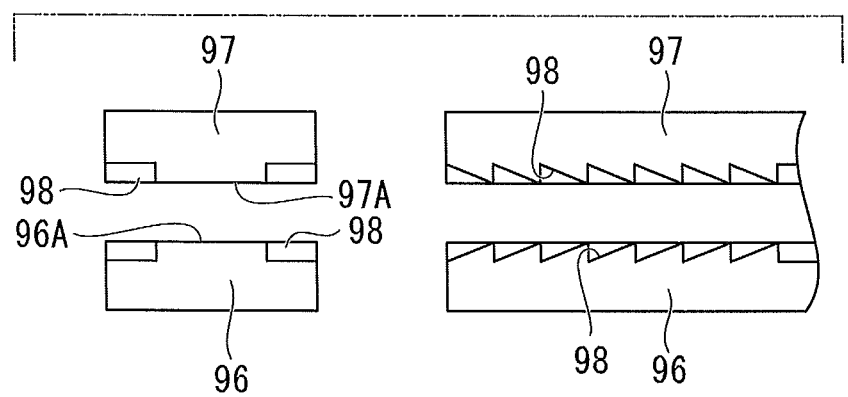
FIG. 17 is a view showing a pair of jaws in another modification of the medical instrument relating to the first embodiment of the present invention.

As shown in FIG. 17, to prevent the tissue sandwiched by the pair of jaws 96 and 97 from sliding and falling out due to body fluids, a plurality of engaging protrusions 98 may be provided. The engaging protrusions 98 are formed so as to protrude from suture faces 96A and 97A on which the anvil member and the cartridge are disposed. A part of the sandwiched tissue is deformed to enter between the adjacent engaging protrusions 98 and is engaged. In the engaging protrusions 98, a rising angle of the distal end side is smaller than that of the proximal end side. For this reason, if the entering tissue is adapted to move to the distal end side, the engaging protrusions 98 bite into the tissue and suppress the movement to the distal end side. That is, the tissue is inhibited from dropping out of the pair of jaws.

Figure 18:
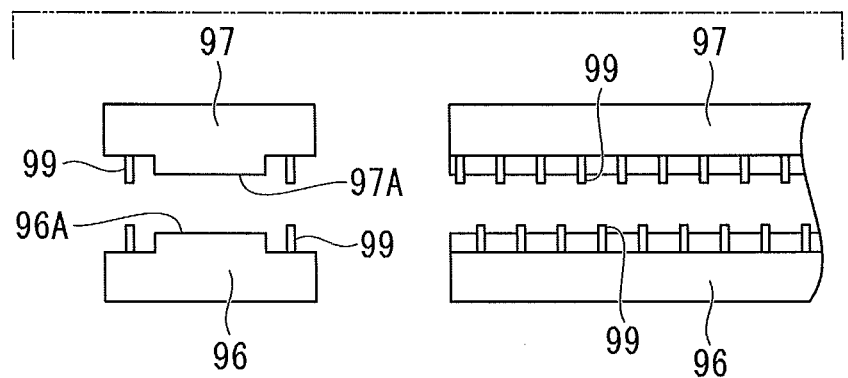
FIG. 18 is a view showing a pair of jaws in another modification of the medical instrument relating to the first embodiment of the present invention.

The engaging protrusions 98 are not limited to the foregoing. Pin-shaped engaging protrusions 99 as in FIG. 18 may be provided. Further, as shown in FIG. 18, the engaging protrusions 99 may be alternately disposed at the sides of the jaw 96 and the jaw 97, and thereby the engaging protrusions 99 may be formed so as not to interfere with one another during suture manipulation by which the suture faces 96A and 97A come closest to each other. In this case, the engaging protrusions 99 may be formed so as to protrude more than the suture face to some extent.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A medical instrument comprising:
    an insertion unit having flexibility, the insertion unit extending along a longitudinal axis;
    a treatment unit having a first grasping member provided at a distal end of the insertion unit and a second grasping member configured to approach and separate from the first grasping member;
    a parallel link having a first connecting site rotatably connected to the first grasping member and a second connecting site rotatably connected to the second grasping member and connected to the first connecting site, such that the first grasping member and the second grasping member are maintained to be substantially parallel to each other in a position where the first grasping member and the second grasping member approach each other and a position where the first grasping member and the second grasping member separate from each other;
    a rotating body configured to be rotatably installed on a rotation shaft fixed to the first grasping member;
    an open-close link having a first end rotatably connected to a first rotation shaft provided on the second grasping member and a second end rotatably connected to a second rotation shaft provided on the rotating body at a distance from the rotation shaft, the second end being connected to the first end;
    a manipulating member configured to rotate the rotating body; and
    a manipulation unit provided at a proximal end of the manipulating member,
    wherein, while the rotating body rotates about the rotation shaft by the manipulating member being pulled toward the manipulation unit by the manipulation unit and moves the second connecting site of the parallel link toward a proximal end of the treatment unit, the rotating body causes the first grasping member and the second grasping member to approach each other while the second rotation shaft approaches an imaginary straight line connecting axes of the rotation shaft and the first rotation shaft.

2. The medical instrument according to claim 1, wherein the rotating body is a disc-shaped pulley.

3. The medical instrument according to claim 2,
    wherein the manipulating member has flexibility, is disposed in the insertion unit, and is connected to the rotating body and the manipulation unit.

4. The medical instrument according to claim 1,
    wherein the manipulating member has flexibility, is disposed in the insertion unit, and is connected to the rotating body and the manipulation unit.

5. The medical instrument according to claim 1, further comprising a grasping member link whose first end is rotatably connected to the first rotation shaft and whose second end is rotatably connected to a third rotation shaft provided on the first grasping member,
    wherein, when the rotating body is rotated in a predetermined direction, the first grasping member and the second grasping member approach each other while a distance between an intersection, at which an imaginary straight line connecting the axis of the first rotation shaft and an axis of the second rotation shaft intersects an imaginary straight line connecting an axis of the third rotation shaft and the axis of the rotation shaft, and the axis of the rotation shaft is reduced.

6. The medical instrument according to claim 5, further comprising a position unit configured to position the first grasping member and the second grasping member in a predetermined positional relation when the first grasping member and the second grasping member approach each other.

7. The medical instrument according to claim 6, wherein the position unit comprising:
    a first contacting face provided on the first grasping member; and
    a second contacting face provided on the second grasping member, the second contacting face being configured to come into contact with the first contacting face when the first grasping member and the second grasping member approach each other.

8. The medical instrument according to claim 1, further comprising a holder configured to hold a proximal end of the second grasping member at a predetermined position when the first grasping member and the second grasping member approach each other.

9. The medical instrument according to claim 1, further comprising a cutter configured to advance and retreat in a longitudinal direction of the treatment unit and to cut off tissue sandwiched between the first grasping member and the second grasping member,
    wherein a cartridge that contains staples is exchangeably attached to the first grasping member, and the first grasping member and the second grasping member function as a stapler.

* * * * *